United States Patent [19]
Myers

[11] Patent Number: 5,716,397
[45] Date of Patent: Feb. 10, 1998

[54] ANNULOPLASTY DEVICE WITH REMOVABLE STIFFENING ELEMENT

[75] Inventor: David J. Myers, Garden Grove, Calif.

[73] Assignee: Medtronic, Inc., Minneapolis, Minn.

[21] Appl. No.: 761,688

[22] Filed: Dec. 6, 1996

[51] Int. Cl.[6] .......................................... A61F 2/24
[52] U.S. Cl. .................... 623/2; 623/900; 623/1; 606/1
[58] Field of Search .................... 623/1, 2, 900; 606/1

[56] References Cited

U.S. PATENT DOCUMENTS

| | | | |
|---|---|---|---|
| 4,042,979 | 8/1977 | Angell | 623/2 |
| 4,917,698 | 4/1990 | Carpentier et al. | 623/2 |
| 5,061,277 | 10/1991 | Carpentier et al. | 623/2 |
| 5,064,431 | 11/1991 | Gilbertson et al. | 623/2 |
| 5,306,296 | 4/1994 | Wright et al. | 623/900 |
| 5,522,884 | 6/1996 | Wright | 623/2 |

OTHER PUBLICATIONS

Medtronic Product Specification: "Duran Flexible Annuloplasty Ring", date Unknown.

Baxter Product Specification: "Carpentier–Edwards Prosthetic Rings Models 4500 and 4400 for Tricuspid and Mitral Valvuloplasty", 1991.

Baxter Product Specification: "Cosgrove–Edwards Annuloplasty System", Mitral Model 4600 w/Handle/Lanyard for Mitral Valvuloplasty, 1994.

*Primary Examiner*—Paul B. Prebilic
*Attorney, Agent, or Firm*—Harry G. Weissenberger

[57] ABSTRACT

A fully flexible annuloplasty ring is temporarily stiffened during implantation by inserting a withdrawable stiffening wire into a lumen of the ring. The annuloplasty ring has a lumen which is able to hold the stiffener prior to and during insertion. The stiffener includes a portion extending out of the lumen which can be pulled to withdraw the stiffener once the implant has been implanted.

15 Claims, 5 Drawing Sheets

ANNULOPLASTY DEVICE WITH REMOVABLE STIFFENING ELEMENT

FIELD OF THE INVENTION

This invention relates to annuloplasty rings or bands for use in heart valve surgery, and more particularly to a flexible annuloplasty ring or band which incorporates a removable stiffening element.

BACKGROUND OF THE INVENTION

Human heart valves, such as the mitral and tricuspid valves are sometimes damaged by diseases or by aging which cause problems with the proper function of the leaflets and/or the sub-valvular apparatus attached to the leaflets. Often, degenerative disease causes the valve annulus to enlarge to the point where the leaflets attached to it cannot fully close. This inability to completely close, a condition called valve incompetence, eventually requires surgical correction either by valve repair procedures or by valve replacement. In the former, also called valvular annuloplasty, various types of ring-shaped devices or bands fashioned from biocompatible cloth-like materials are sewn to the distended annulus. By properly sizing and implanting the annuloplasty ring or band, the surgeon can restore the valve annulus to its normal, undilated, circumference.

Annuloplasty rings or bands are typically of two types, either completely flexible or stiff and comparatively rigid. An example of the former is the Duran Ring or the Cosgrove Band, while an example of the latter is the Carpentier Ring.

The Carpentier Ring consists of an open wire element completely covered with cloth. The wire is somewhat stiff yet resiliently deformable and is not intended to be removable from the cloth covering. This ring is particularly useful in the repair of heart valves that have lost annular elasticity from, e.g., the chronic effects on the mitral valve of rheumatic fever. Due to their permanent rigidity, the Carpentier Rings lie flat and maintain their somewhat oval shape during handling by the surgeon at time of implantation. Although the Carpentier Ring's rigid oval shape is claimed to enhance the competence of the repaired valve, the rigidity also impedes the beneficial flexing movements of the native annulus during the cardiac cycle.

The other major type of annuloplasty ring or band is exemplified by the totally flexible Duran Ring or the Cosgrove Band. These devices consist of a soft core of silicone rubber impregnated with a radiopaque salt, e.g. barium sulfate, completely enclosed by a sheath of biocompatible cloth. These devices are completely flexible and useful in the repair of heart valves whose annuli have become enlarged in diameter but are not stiffened and inflexible. Because of its flexibility, the Duran Ring is supported during implantation by a holder which is subsequently removed before tie-off of the implanting sutures, as shown in U.S. Pat. No. 5,011,481. One problem with this approach is that the holder does not completely restrain the entire circumference of the ring and does not prevent the flexible ring from bunching or forming pleats as the implanting sutures are tied off. The Cosgrove Band, like the Duran Ring, is totally flexible; however, bunching of the Cosgrove Band is prevented by the mounting of the device on a rigid support (U.S. Pat. No. 5,041,130) subsequently removed after the implanting sutures are tied off. Neither the Duran Ring or the Cosgrove Band can be tested for competence in the ideal systolic shape as can the rigid Carpentier Ring. Hybrids of the foregoing types of rings have also been proposed, as for example the Sculptor ring in which the anterior segment (which corresponds to the intertrigone area) is rigid but the posterior segment is totally flexible and also fitted with drawstrings to finely adjust its diameter. Although this complex ring can be used in the same circumstances as a Duran Ring, it mitigates but does not overcome the handling difficulties associated with flexible rings.

To overcome the deficiencies of the above-described ring/band structures, it would be ideal for an annuloplasty device to be stiff during handling and implantation, but then become totally flexible immediately after implant. Also, upon the desire of the surgeon to make it so, the ring could be left rigid for testing the adequacy of his repair (such as injecting fluid through the opening between the leaflets); this is best conducted with the annulus in its normally oval shape during systole. If competency is adequate, the ring is then made totally flexible by means of the invention described below.

SUMMARY OF THE INVENTION

The present invention provides temporary stiffening for an annuloplasty implant by installing in a fully flexible ring, preferably in a separate lumen, a resilient wire or similar element which maintains the device in its prescribed shape, preferably an oval, but can be removed therefrom by pulling on an end of the stiffening element that protrudes from the ring or band.

DESCRIPTION OF THE PREFERRED EMBODIMENT

Figure 1:
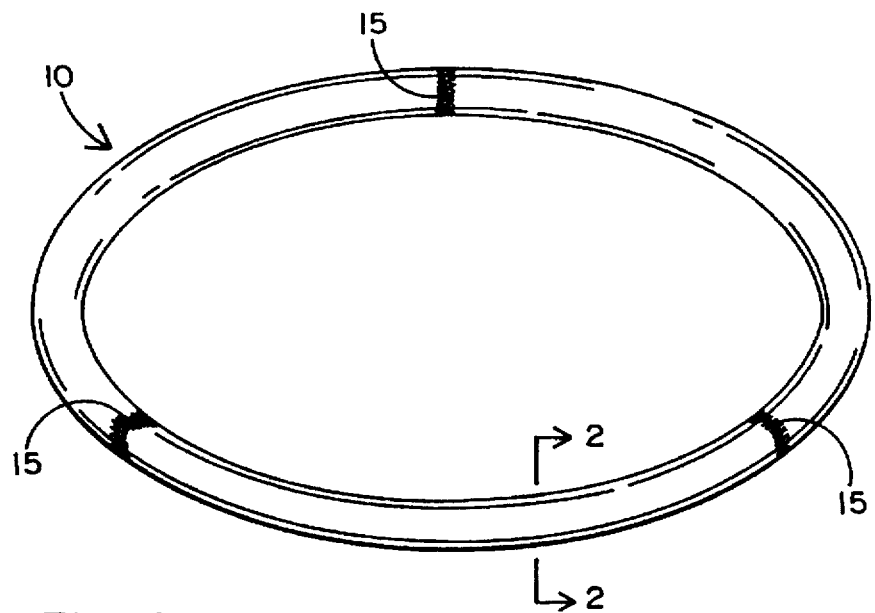
FIG. 1 is a plan view of a conventional Duran ring.
Figure 2:
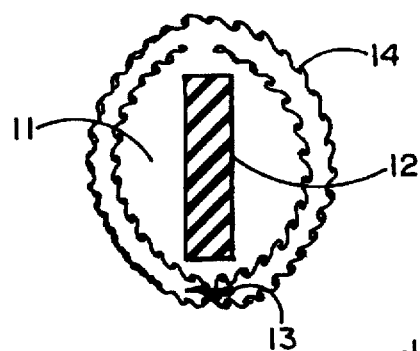
FIG. 2 is a section along line 2—2 of FIG. 1.
Figure 3:
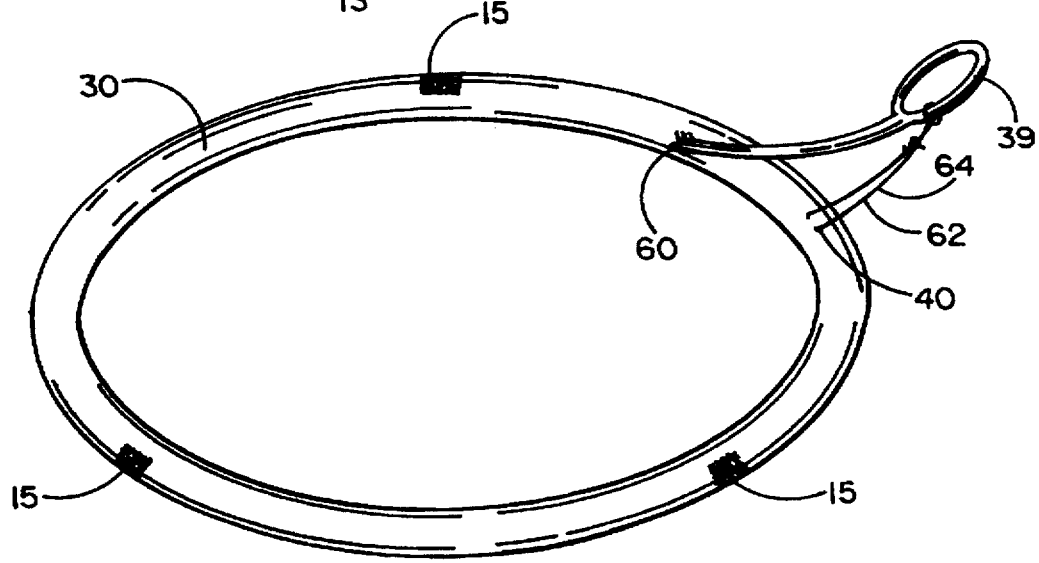
FIG. 3 is a perspective view of an annuloplasty ring in accordance with the present invention.

FIGS. 1 and 2 illustrate a conventional Duran Ring construction. Like the Cosgrove Band illustrated in FIGS. 6e–g, the Duran Ring 10 has a lumen 11 containing a generally rectangular inner core 12 of radio-opaque silicone rubber which is radially completely flexible. The radiopacity of the core 12 allows the presence and functioning of the implant to be monitored after completion of the implant sugery. The core 12 is completely enclosed by a sheath 14 of biocompatible cloth. The sheath 14 is made by folding a cloth sheet around the core 12 and sewing the folded ends together at 13. The combination of the core 12 and sheath 14 result in a ring which is completely flexible yet essentially nonextensible. This property allows the annuloplasty ring or band, when implanted in the heart, to prevent the valve annulus from becoming distended, without significantly impeding the natural motion of the annulus. The ring 10 has three trigone markers 15 sewn thereon at 120° intervals to assist the surgeon in the placement of sutures.

One of the disadvantages of the fully flexible ring 10 is that it needs to be supported in its proper shape during the implantation procedure. This is typically accomplished by mounting the ring 10 on a holder such as that shown in U.S.

Pat. No. 5,011,481, which is removed once the implant sutures are in place. Such holders, however, do not prevent the ring 10 from bunching or pleating when the implant sutures are tied off, if the sutures are not precisely placed.

In accordance with the present invention, the need for a holder is obviated by temporarily stiffening the annuloplasty ring or band itself during the implant procedure, and then removing the integral stiffening element after the sutures have been tied off.

Figure 4:
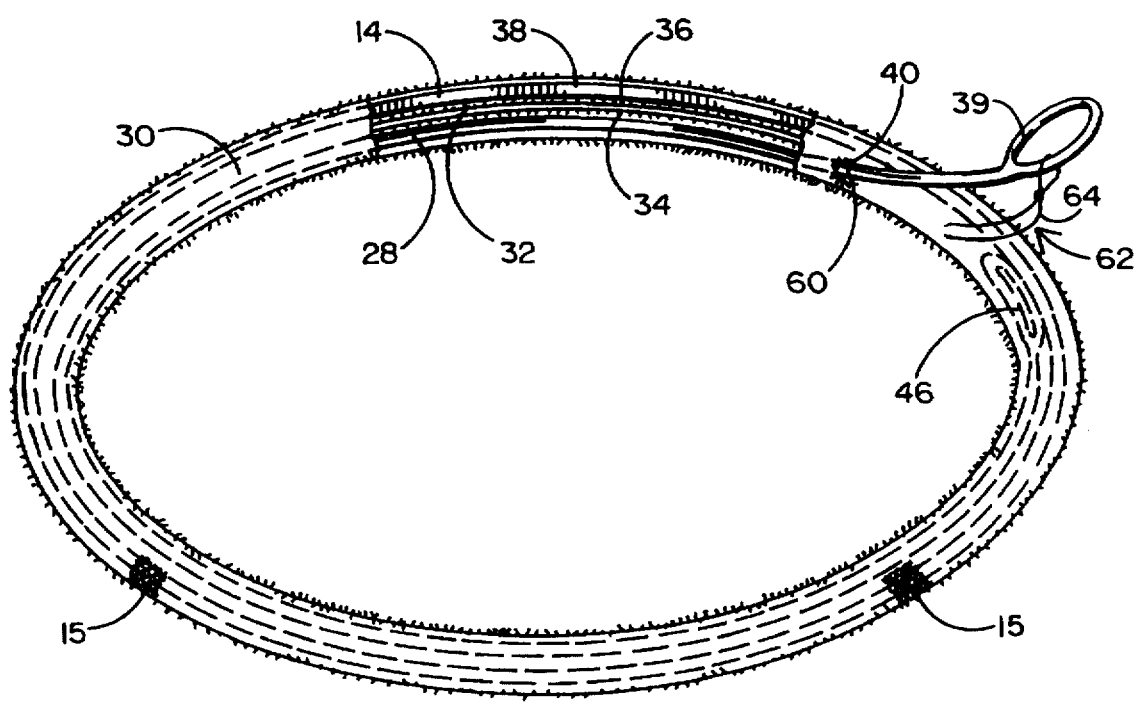
FIG. 4 is a plan view, partially cut away of the ring of FIG. 3.
Figure 5:
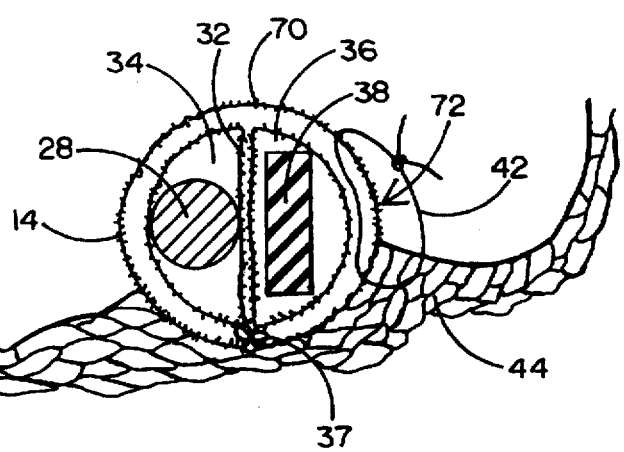
FIG. 5 is a section along line 5—5 of FIG. 4.

FIGS. 3–7 illustrate the present invention using a removable stiffener 28. In FIGS. 4 and 5, it will be seen that the interior of the inventive ring or band 30 is preferably divided by an inner cloth wall 32 into a stiffener lumen 34 and a radiopaque core lumen 36. The core lumen 36 contains the silicone rubber core 38 and receives the implant sutures therethrough as does the ring 10 of FIGS. 1 and 2. The folds of the cloth 14 and the ends of the cloth wall 32 are sewn together at 37.

The stiffener lumen 34 of the inventive ring or band 30 contains the stiffener 28. The position of stiffener 28 beside the core 38 and separated therefrom assures that the stiffener 28 will not interfere with the placement of sutures through the core 38, and that conversely, the sutures will not interfere with the eventual removal of the stiffener 28.

The stiffener 28 extends substantially around the entire circumference or extent of the ring or band 30 and terminates in a grasping portion 39 which protrudes through the cloth sheath 14. The grasping portion 39 may take the form of a loop or hook, or any other form that lends itself to being grasped by a tool or by the surgeon's hand, and which prevents the grasping portion 39 from being pushed into the ring or band 30 as explained below in connection with FIG. 7.

The stiffener 28 must satisfy several criteria. For one, it must be fully insertable into the ring or band 30 through an opening 40 (FIG. 7) without snagging or tearing the cloth sheath 14 or inner wall 32. Secondly, it must be withdrawable with a minimum of stress on the ring or band 30 to prevent damage to the sutures 42 which secure the ring or band 30 to the annulus 44 (FIG. 5) when the surgery is complete. Thirdly, it must be stiff enough to maintain the ring or band 30 in a flat plane during implantation but flexible enough to allow the deformation inherent in withdrawal. In a preferred embodiment, these objectives are achieved by using for the stiffener 28 a length of Haynes Alloy #25 wire. This wire has a thickness of about 750 μm and would have a length of about 10 cm for a 29 mm Duran ring.

The end or ends 46 of the stiffener wire 28 opposite the grasping portion 39 are preferably formed into a generally bulbous shape to prevent the wire 28 from snagging the cloth 12 when it is threaded through the lumen 34 during manufacture of the ring or band 30. The stiffener wire 28 itself is preferably polished to a very smooth surface, so that it will easily slide in the lumen 34 during insertion and withdrawal.

Figure 6A:
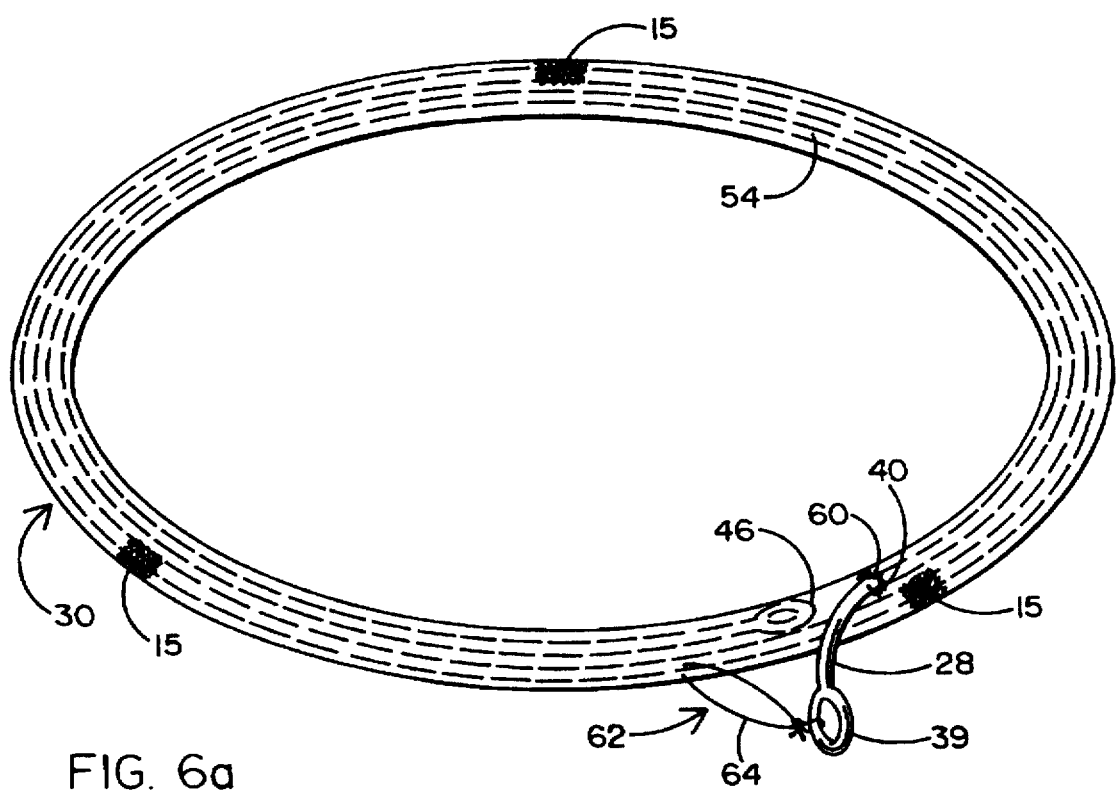
FIGS. 6a–g are plan views illustrating various positionings of the stiffener in rings and bands.
Figure 6B:
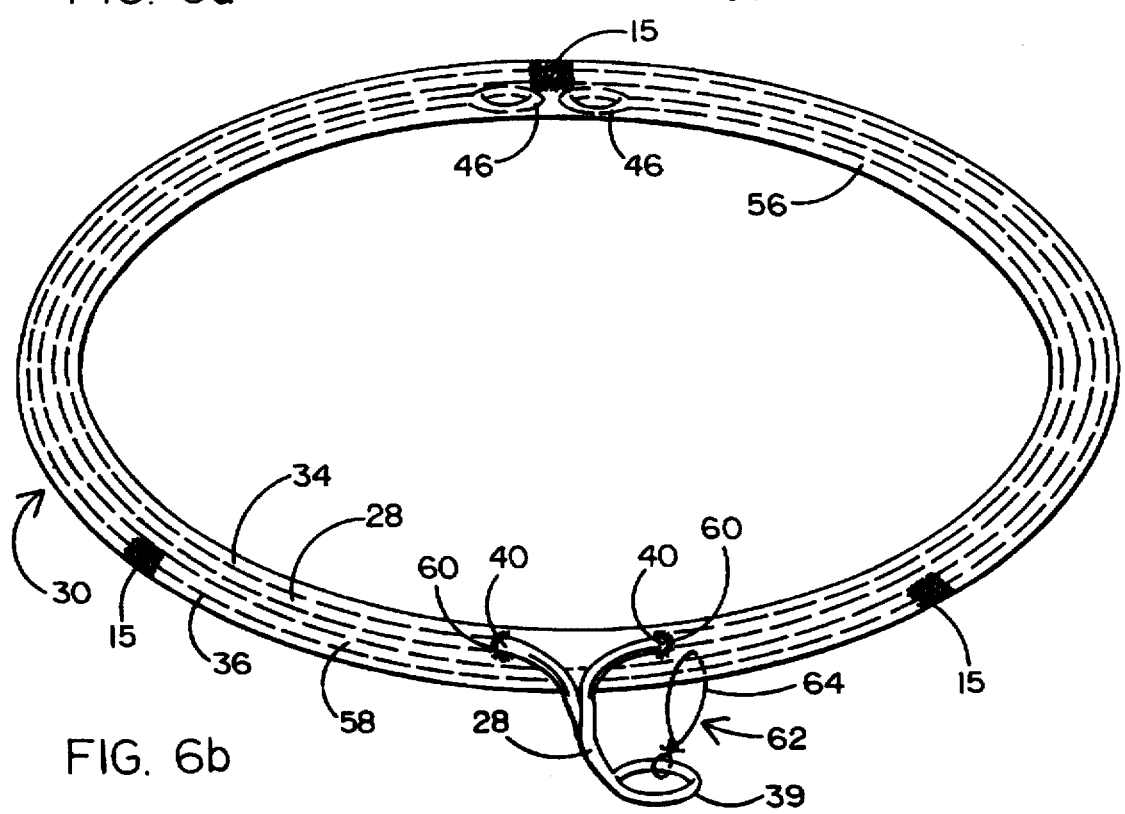
Figure 6C:
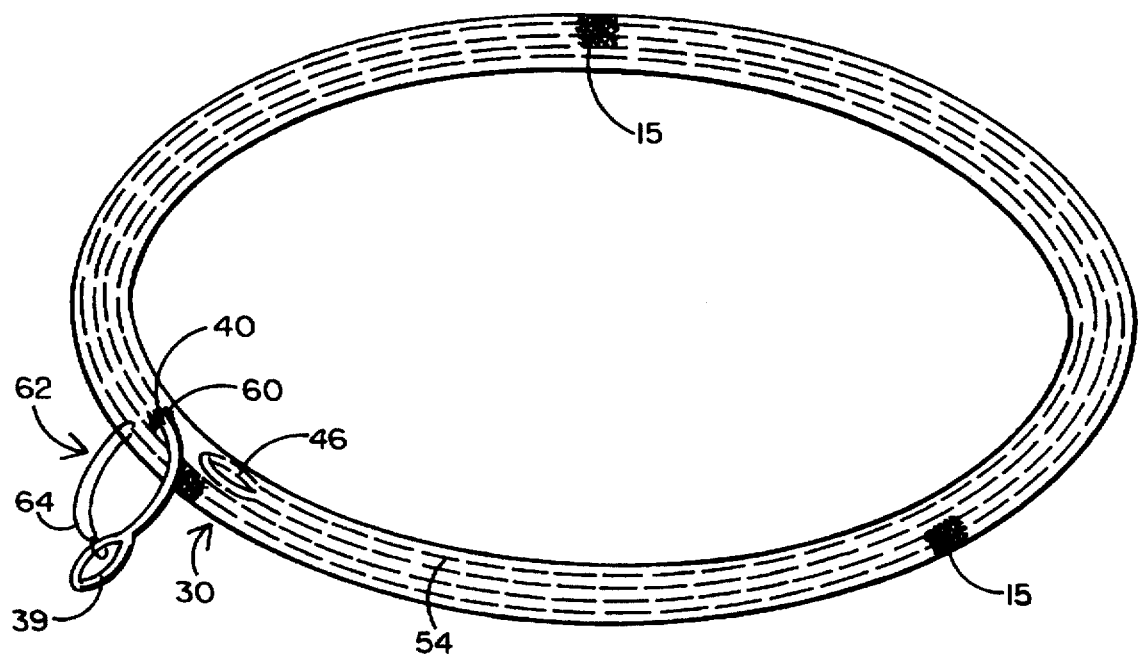
Figure 6D:
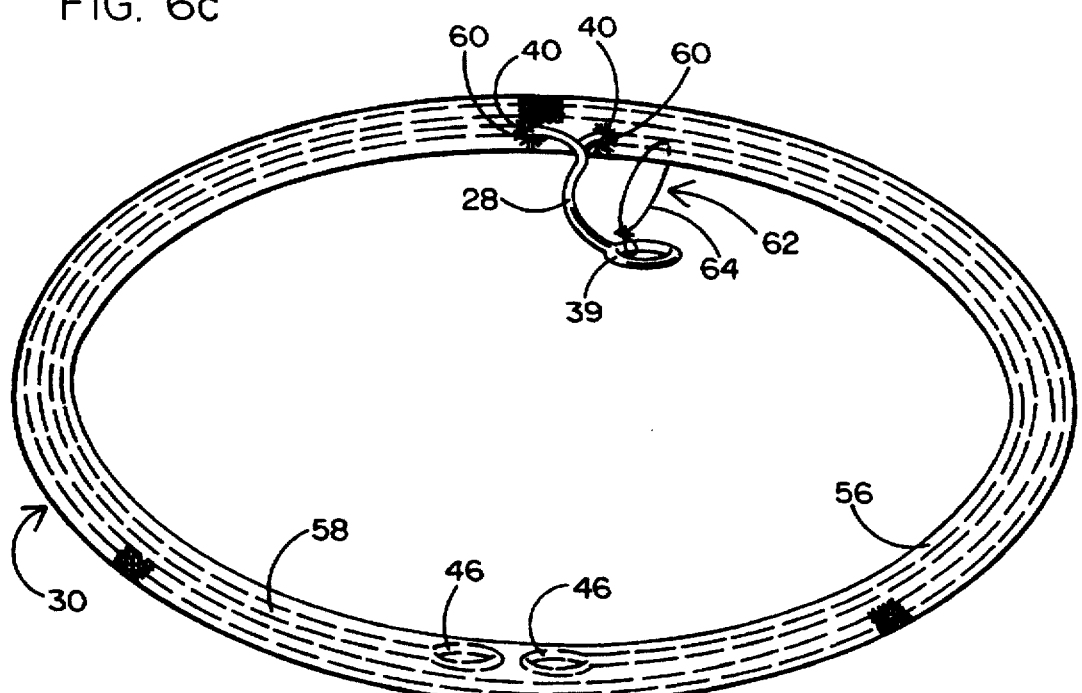
Figure 6E:
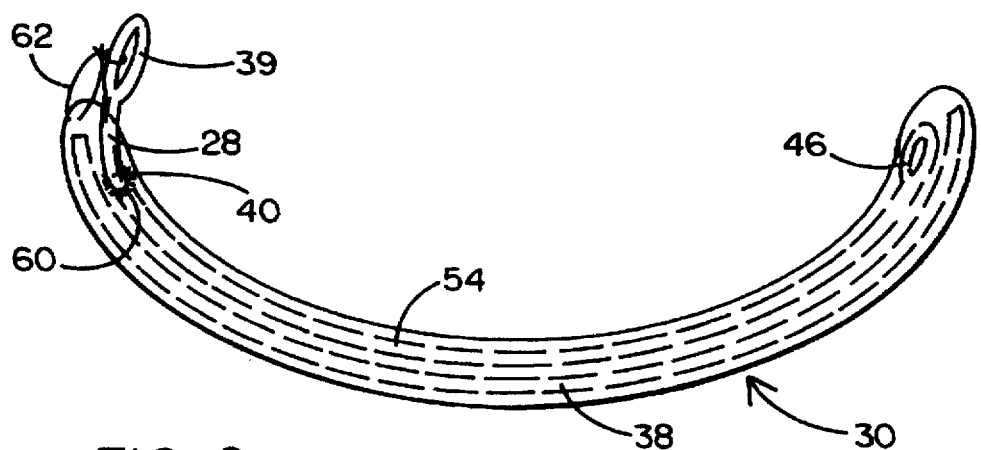
Figure 6F:
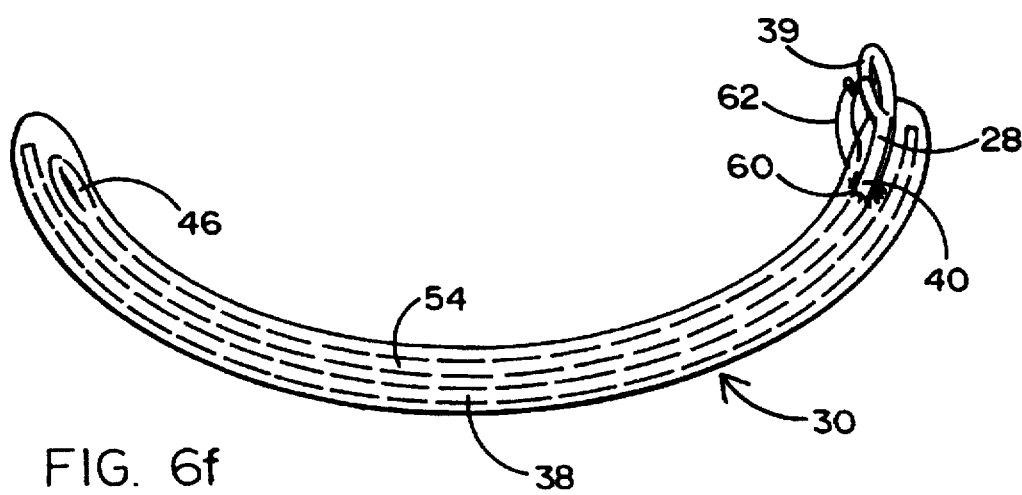
Figure 6G:
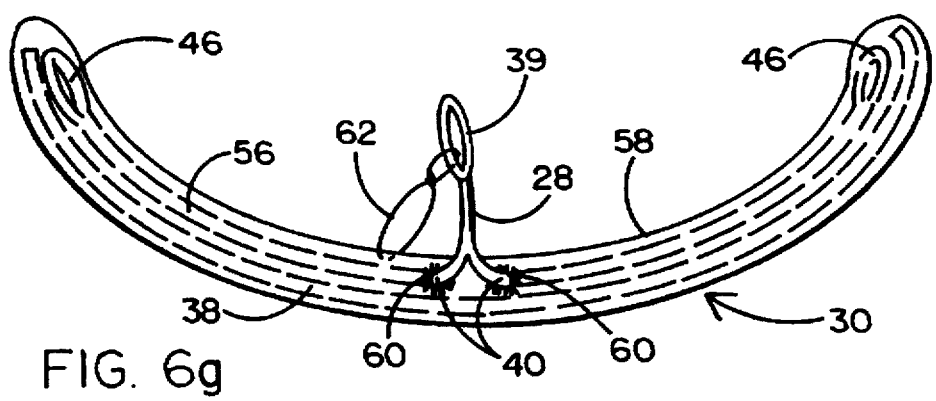

FIGS. 6a–g illustrate various preferred ways in which a stiffener 28 can be placed in a ring (FIGS. 6a–d) or band (FIGS. 6e–g). The stiffener 28 may have a single leg 54 which extends from the grasping portion 39 although the entire length of the ring 50 or band 30 (FIGS. 6a, 6c, 6e and 6f). Alternatively, the stiffener 28 may have a pair of legs 56, 58 extending in opposite directions from a centrally located grasping portion 39 (FIGS. 6b, 6d and 6g). The grasping portion may be located in the upper or lower center of the ring or the center of the band (FIGS. 6b, 6d and 6g); on the right side or end of the ring or band 30 (FIGS. 6a and 6f); on their left side or end (FIGS. 6c and 6e); or in the generally 1 o'clock position shown in FIGS. 3 and 4. Typically, because the legs 56, 58 of the two-leg embodiments are shorter, these embodiments tend to place less stress on the ring or band 30 during removal of the stiffener 28.

Figure 7:
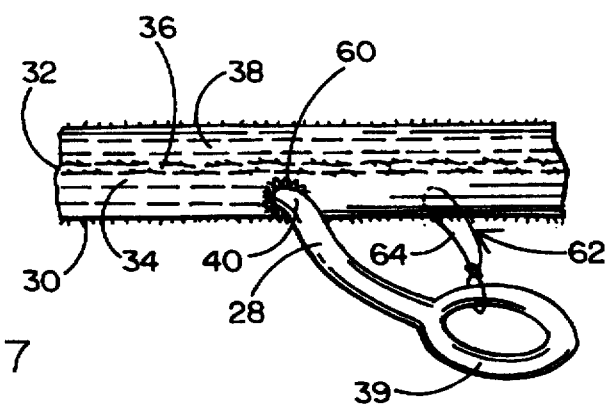
FIG. 7 is a detailed elevation of the stiffener grasping portion.

FIG. 7 details the preferred arrangment of the opening 40 which receives the stiffener 28. In order to prevent snagging or tearing of the cloth 12 during insertion or removal of the stiffener 28, a reinforcement or trim 60 is added to the cloth 14 around the circumference of the opening 40. In addition, a security suture 62 is preferably placed through the grasping portion 39 and core 38 to prevent premature removal of the stiffener 28. The suture 62 is so attached to the grasping portion 39 that all of the suture 62 will come out with the stiffener 28 when the suture 62 is cut at 64 and the stiffener 28 is withdrawn from the ring or band 30.

Because surgeons unfamiliar with the construction of the inventive ring or band 30 may accidentally try to suture the ring or band 30 through the stiffener lumen 34, it is desirable to provide indicia to delineate the core lumen 36 through which the sutures should be made. The indicia can be any of a variety of visual features, for example, an additional suture may be placed lengthwise of the ring or band 30 at 70 in FIG. 5 (the suture at 37 is already visible). A preferred method, however, is to apply a distinctive color to the portion of the sheath 14 which surrounds the core lumen 36, i.e. the right half 72 of the sheath 14 in FIG. 5.

It will be seen that the present invention provides an effective way of temporarily stiffening a Duran ring during the implantation process, and then restoring its full flexibility once the implantation is completed.

It should be understood that the exemplary annuloplasty ring with removable stiffener described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. An annuloplasty implant for implantation into a heart, comprising:
    a) a substantially annular, fully flexible implant for annuloplastic surgery, said flexible implant having a lumen formed therein; and
    b) a stiffening element disposed in said lumen substantially throughout the length of said implant;
    c) said stiffening element including a portion extending outwardly of said lumen;
    d) said stiffening element withdrawable such that it can be withdrawn from said lumen upon completion of said implantation.

2. The implant of claim 1, in which said outwardly extending portion is at one end of said stiffening element.

3. The implant of claim 1, in which said outwardly extending portion is located substantially centrally of said stiffening element.

4. The implant of claim 1, in which said flexible implant has a pair of lumens horizontally spaced from each other along said flexible implant, said stiffening element being disposed in one of said lumens, and a suturing core being disposed in another of said lumens, so as to cause said suturing core to be held horizontally spaced from said stiffening element.

5. The implant of claim 4, further comprising indicia on the outside of said other of said lumens to visually identify the location of said lumen.

6. The implant of claim 1, in which at least one end of said stiffening element is sufficiently rounded to prevent it from snagging the material of said flexible implant when said stiffening element is inserted into said lumen.

7. The ring of claim 1, in which said stiffening element is polished.

8. The implant of claim 1, in which said stiffening element is formed from a material having the property of being flexible enough to allow withdrawal.

9. The implant of claim 1, in which said stiffening element can be inserted into said lumen through an opening in the wall thereof, the circumference of said opening being reinforced to prevent damage to said implant when said stiffening element is inserted or withdrawn through said opening.

10. The implant of claim 1, in which said stiffening element is held to said implant by a suture which is so tied to said stiffening element that said suture is completely removed from said implant by withdrawal of said stiffening element when said suture is properly cut.

11. A method of temporarily stiffening an annuloplasty implant during implantation, comprising the steps of:

a) providing a flexible annuloplasty implant having at least one lumen;

b) placing into said lumen, prior to implantation, a stiffening element having a portion protruding from said implant to allow said stiffening element to be grasped from the outside of said implant;

c) implanting said flexible implant by suturing said flexible implant to the tissue in which it is to be implanted; and d) withdrawing said stiffening element from said implant following said suturing step.

12. The method of claim 11, in which said stiffening element is a wire, and said method comprises the further step of polishing said wire prior to placing said wire into said lumen.

13. The method of claim 11, in which said implant has at least two lumens, said stiffener is placed into one of said lumens, and said suturing step is performed by placing sutures through the other of said lumens.

14. The method of claim 13, in which said implant is of curved shape, and said one of said lumens is positioned on the inside of the curve.

15. The method of claim 13, further comprising the step of marking, prior to said suturing step, said implant to visually indicate the position of said other of said lumens.

* * * * *